United States Patent [19]

van der Jagt

[11] Patent Number: Plant 6,482

[45] Date of Patent: Dec. 20, 1988

[54] CHRYSANTHEMUM NAMED "BRONZE REPIN"

[75] Inventor: Martinus van der Jagt, Ter Aar, Netherlands

[73] Assignee: Chrysanthemum Breeders Assoc., N.V., Curacao, Netherlands Antilles

[21] Appl. No.: 19,183

[22] Filed: Feb. 25, 1987

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Parkhurst & Oliff

[57] ABSTRACT

A new and distinct cultivar of Chrysanthemum plant named Bronze Repin, bearing medium sized bronze blossoms with a bronze/green center and a performance of twenty days.

3 Drawing Sheets

BACKGROUND OF THE NEW PLANT

The new plant of the present invention relates to the Chrysanthemum genus.

ORIGIN AND HISTORY OF THE PLANT

The new plant according to the present invention comprises a new and distinct cultivar of Chrysanthemum plant which is a color mutant of Chrysanthemum named Repin. The new cultivar was discovered by Martinus van der Jagt at Paradijsweg 88, Ter Aar, Holland. The new cultivar has been asexually reproduced by cuttings at the same location, and has been found to retain its distinctive characteristics through successive propagations.

SUMMARY OF THE NEW PLANT

The present invention is a new and distinct variety of Chrysanthemum of a medium sized bloom and bronze color.

BRIEF DESCRIPTION OF THE DRAWINGS

The present new and distinct Chrysanthemum cultivar is shown in the accompanying drawings, the color being as nearly true as possible with color photographs of this type.

Sheet 1 shows the full bloom of the new cultivar;

Sheet 2 shows various stages of bloom of the new cultivar; and

Sheet 3 shows the foliage and petiole of the new cultivar.

DESCRIPTION OF THE NEW PLANT

This new variety of Chrysanthemum is of the botanical classification *Chrysanthemum morifolium,* named Bronze Repin. When grown in the vicinity of Ter Aar, Holland, it has a response time of approximately ten weeks. This new variety produces medium sized bronze blooms with a bronze/green center having a performance of twenty days. This new variety of Chrysanthemum has been found to retain its distinctive characteristics throughout successive propagations and may be planted under conventional greenhouse conditions in Holland between weeks 1 and 34.

The following is a description of the plant and characteristics that distinguish it over related known varieties and its antecedents:

Botanical classification: *Chrysanthemum morifolium.*

Bud:
- *Size.*—Large (cross section: 1.6 cm, height: 1.2 cm).
- *Form.*—Round and a flat top.
- *Outside color.*—Greyed orange 172A.

Bloom:
- *Size.*—Medium to large.
- *Fully expanded.*—7.5-9 cm.
- *Borne.*—Mostly single, sometimes several.
- *Stems.*—Strong.
- *Forms.*—Single (daisy).
- *Permanence.*—Excellent, 3 weeks (18°-20° C.).

Color:
- *Center of flower (disk floret).*—Greyed orange 167A.
- *Base of petals.*—Greyed orange 167A.
- *Inside of petals.*—Greyed orange 167A.
- *Reverse of petals.*—Greyed orange 167A.
- *Outer petals.*—Greyed orange 167A.
- *Tonality from a distance.*—A bronze daisy with a center of the same color.
- *Discoloration.*—To a greyed orange 167D upon maturity.

Petals:
- *Texture.*—Upperside: Rough. Underside: Rough.
- *Number.*—28-32, two rows.
- *Cross-section.*—Convex, two keels.
- *Arrangement.*—Imbricated.
- *Persistence.*—Excellent, 20 days.
- *Fragrance.*—Chrysanthemum.

Reproductive organs:
- *Stamens.*—Thick, yellow, length: 5 mm.
- *Pollen.*—Appears in large quantity when blooming.
- *Styles.*—Yellow, thick, length: 6 mm.
- *Stigmas.*—Yellow, width approx. 2 mm.
- *Ovaries.*—Enclosed in calyx.

Plant:
- *Form.*—Spray mum meant for erect culture.
- *Growth.*—Vigorous.
- *Height.*—115-120 cm.
- *Peduncle.*—Near the top: 8 cm. Near the middle: 15 cm. Near the bottom: 16 cm.
- *Internodes.*—4 cm.
- *Flowering response.*—10 weeks.

Foliage:
- *Color.*—Upperside: yellow green 147A; underside: yellow green 148A.
- *Size.*—Length: 12 cm. width: 8 cm.

*Quantity.*—30 on the average.

*Shape.*—Pointed, deeply undulated.

*Texture.*—Upperside: Smooth. Underside: Smooth, very hirsute.

*Ribs and veins.*—An average number of ribs, a low number of veins. Upperside: Ribs well defined; veins not. Underside: Ribs well defined; veins not.

*Edge.*—Deeply undulated.

In the description above, color references are made to the "R.H.S. Colour Chart" issued by The Royal Horticultural Society, in association with the Flower Council of Holland, Edition February 1986.

What is claimed:

1. A new and distinct cultivar of Chrysanthemum named Bronze Repin, as described and illustrated in the foregoing specification and accompanying drawings.

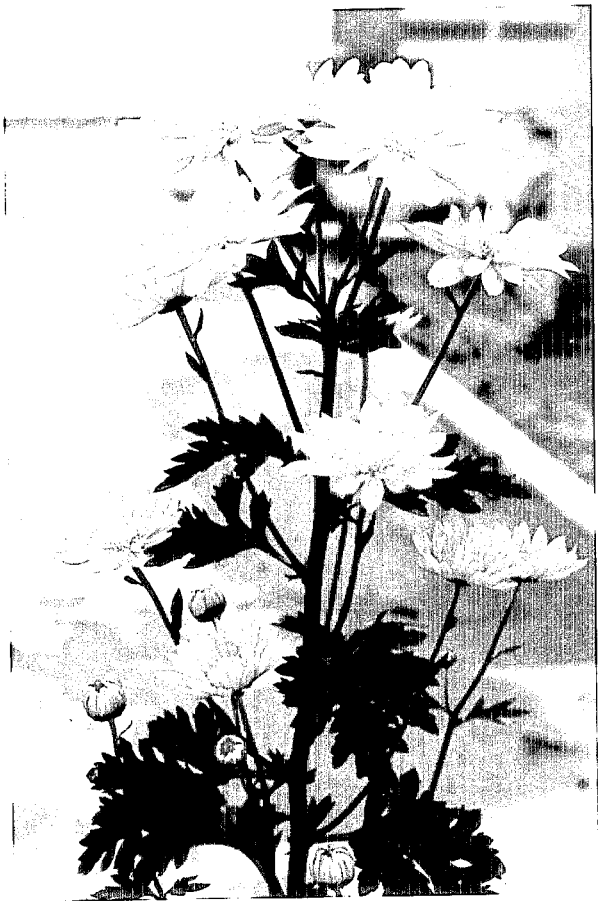

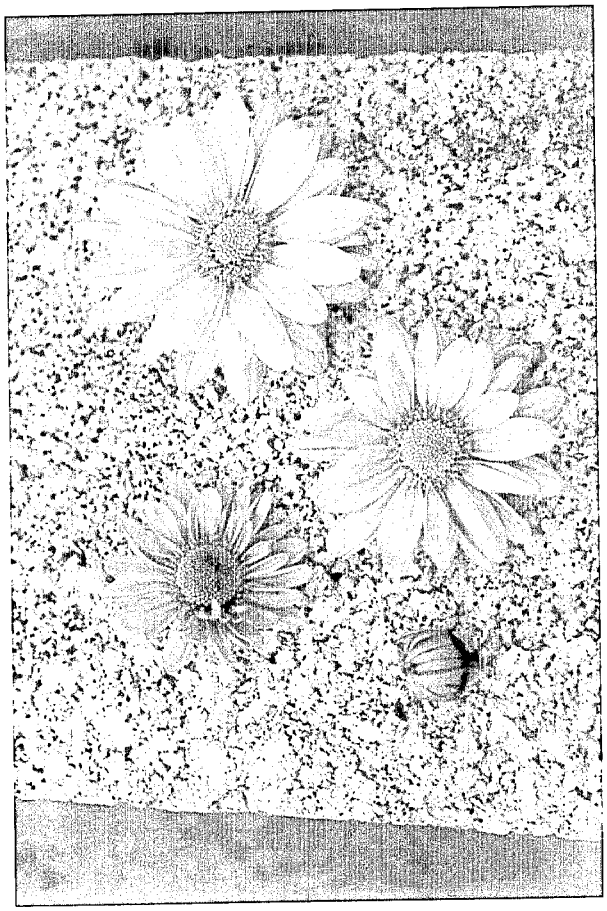

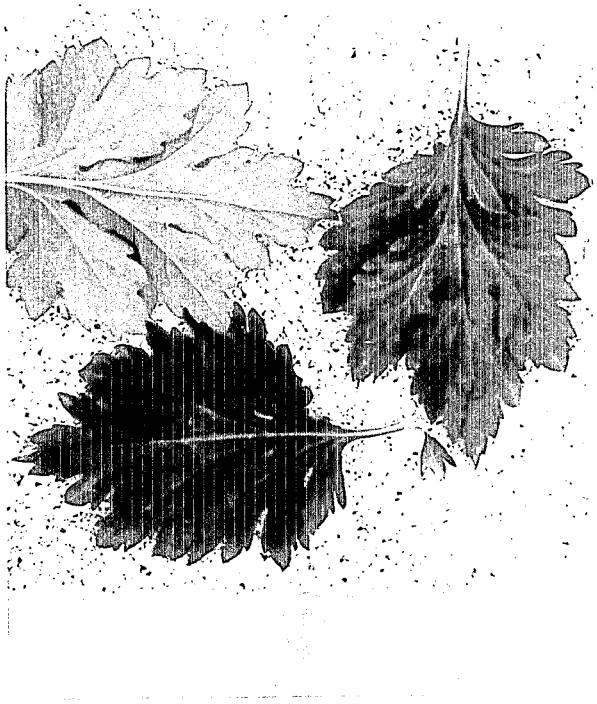

* * * * *